United States Patent [19]
Denz

[11] Patent Number: 5,054,452
[45] Date of Patent: Oct. 8, 1991

[54] METHOD AND APPARATUS FOR DETECTING A FAULT CONDITION OF A LAMBDA PROBE

[75] Inventor: Helmut Denz, Stuttgart, Fed. Rep. of Germany

[73] Assignee: Robert Bosch GmbH, Stuttgart, Fed. Rep. of Germany

[21] Appl. No.: 548,925

[22] PCT Filed: Nov. 21, 1989

[86] PCT No.: PCT/DE89/00727
§ 371 Date: Jul. 30, 1990
§ 102(e) Date: Jul. 30, 1990

[87] PCT Pub. No.: WO90/06431
PCT Pub. Date: Jun. 14, 1990

[30] Foreign Application Priority Data
Nov. 29, 1988 [DE] Fed. Rep. of Germany ....... 3840148

[51] Int. Cl.$^5$ ............................................. F02M 51/00
[52] U.S. Cl. ................................... 123/479; 123/440; 123/489
[58] Field of Search ............... 123/479, 440, 489, 434, 123/480; 204/425, 431; 364/431.03, 431.11, 431.04

[56] References Cited
U.S. PATENT DOCUMENTS

| | | | |
|---|---|---|---|
| 4,528,957 | 7/1985 | Jundt et al. | 123/440 |
| 4,715,343 | 12/1987 | Kinoshita | 123/489 |
| 4,724,814 | 2/1988 | Mieno et al. | 123/479 |
| 4,724,815 | 2/1988 | Mieno et al. | 123/479 |
| 4,742,808 | 5/1988 | Blümel et al. | 123/489 |
| 4,780,826 | 10/1988 | Nakano et al. | 364/431.03 |
| 4,797,828 | 1/1989 | Suzuki et al. | 364/431.04 |
| 4,850,325 | 7/1989 | Abe et al. | 123/479 |
| 4,951,632 | 8/1990 | Yakuwa et al. | 123/479 |
| 4,958,611 | 9/1990 | Uchinami et al. | 123/479 |

Primary Examiner—Raymond A. Nelli
Attorney, Agent, or Firm—Walter Ottesen

[57] ABSTRACT

In a heatable lambda probe, the probe voltage is first measured with the heater switched off and then with the heater switched on. The difference between the two voltages is formed and, when it exceeds a predetermined threshold difference, a shunt signal is output which indicates that the probe is not yet ready for operation. Otherwise, the system is examined for readiness for closed-loop control in the conventional manner.

10 Claims, 4 Drawing Sheets

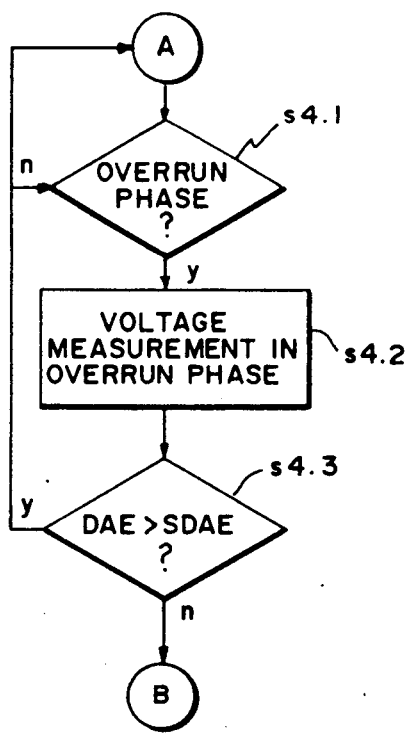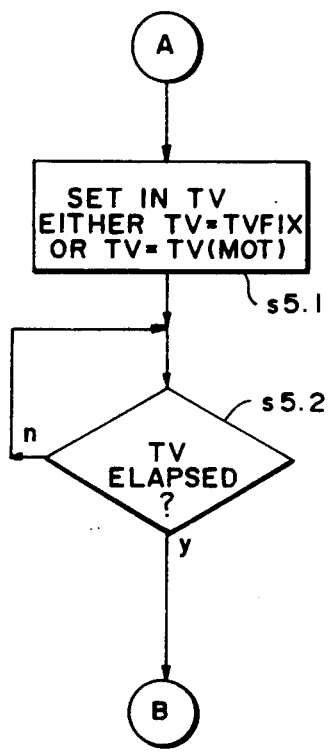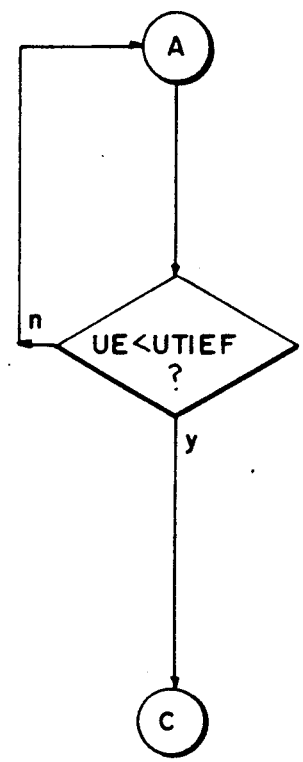
FIG. 4  FIG. 5  FIG. 6
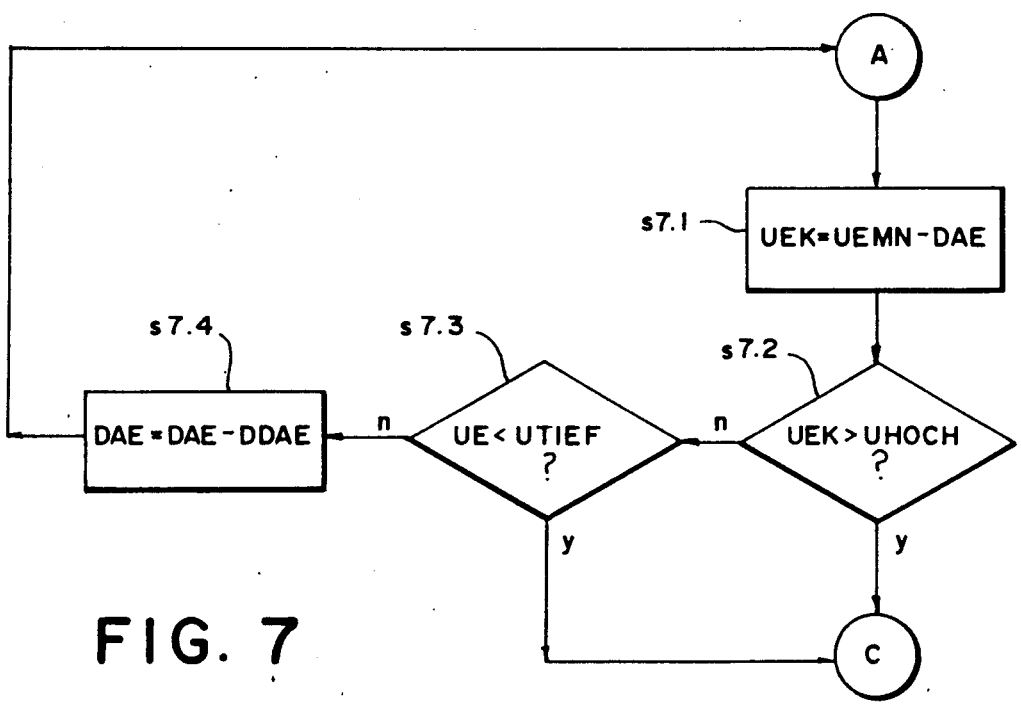
FIG. 7

5,054,452

METHOD AND APPARATUS FOR DETECTING A FAULT CONDITION OF A LAMBDA PROBE

FIELD OF THE INVENTION

The invention relates to a method and an apparatus for detecting a fault condition of a lambda probe and for taking measures following a fault signal which is emitted when the fault condition is detected.

BACKGROUND OF THE INVENTION

Such methods and apparatus are known, for example, from U.S. Pat. No. 4,528,957 and U.S. Pat. No. 4,742,808. In both methods, it is indirectly investigated whether the monitored probe exhibits a sufficiently high temperature for reliable lambda value measurements. If this is not the case, the probe is considered not to be operationally ready and the lambda value is not closed-loop controlled but open-loop controlled. Only when the operating temperature is sufficiently high and operational readiness is thus detected, the lambda value is adjusted by closed-loop control.

In the method according to U.S. Pat No. 4,528,957, a counter voltage is connected to the probe voltage via a known resistance and it is monitored whether the resulting voltage leaves a predetermined range, that is whether it exceeds a threshold voltage for lambda values for rich mixtures or drops below a threshold voltage for lambda values for lean mixtures. As long as the voltage is still within the range, an absence of operational readiness is detected and thus the lambda value is open-loop controlled. In the method according to U.S. Pat. No. 4,742,808, the internal resistance of the probe is directly measured, which is done with the aid of a known load resistance and two voltage measurements. As soon as the measured value drops below a resistance threshold value, the probe is considered to be ready for operation.

It has been found in actual operation that, in spite of such measures, it happens that the probe is detected as ready for operation due to shunts even though this is not the case. This results in poor closed-loop control performance which results in high pollutant emission and poor driving quality.

The invention is based on the object of specifying a reliable method for detecting such a fault condition of a lambda probe. The invention is furthermore based on the object of specifying an apparatus for carrying out such a method.

SUMMARY OF THE INVENTION

The invention is based on the finding that an unwanted shunt can exist between probe heating voltage and probe voltage. In this case, the heating voltage falsifies the voltage generated by the probe. However, the shunt voltage and thus the falsification do not exist when the probe heater is switched off.

It is particularly simple to determine the shunt voltage when the lambda value does not change. This is the case, in particular, before the internal combustion engine starts and during overrun phases. The difference between the probe voltages measured with the heater switched on and switched off directly provides the shunt voltage. If the difference exceeds a predetermined threshold difference value, the fault signal is output.

If the lambda value continuously changes, it is more difficult to determine whether a shunt is present, particularly when a probe with non-linear performance is used, the probe voltage of which changes greatly with a changing lambda value in the range around lambda-=one. If measurements are taken at two successive times, once with the heater switched on and then with the heater switched off and a difference is found between the two measurement values, it is not clear whether this difference is caused by a change in the lambda value or by a shunt or by both. However, this can be established if the switching-off and switching-on is carried out in a pseudo-binary sequence and the measurement values are evaluated by means of a correlation method. If the evaluation shows that an external direct voltage of inadmissible magnitude, which is independent of the respective lambda value, is superposed on the voltage values measured with the heater switched on, the fault signal is output.

Evaluation with the aid of a correlation method is complex but offers the advantage that the amplitude of the shunt voltage can be determined at any time. This makes it possible to use the shunt voltage determined for compensating the measured probe voltage. As a result, a correct probe voltage value is obtained on the basis of which closed-loop control can be effected.

If a simple method is carried out by means of which the amplitude of the shunt voltage cannot be determined in periods in which the lambda value changes, it is of advantage to open-loop control the lambda value as long as the fault signal is present. However, there is then a desire to eliminate the effect of the fault signal as soon as possible. This is done in the simplest way by eliminating the effect of the fault signal after a predetermined period of time has elapsed after the detection of the fault condition. Another possibility consists in waiting until overrun mode is reached. The method for detecting the shunt is then again carried out. If it is found that there is no longer any fault condition, the effect of the previously emitted fault signal is cancelled. The method just mentioned allows a very accurate determination of whether a fault condition still exists. However, a relatively long time can pass until checking becomes possible, namely when no overrun operation occurs for a relatively long time. To cancel the effect of the fault signal, methods are therefore of particular advantage which check whether the probe voltage reaches a predetermined threshold value. If this is the case, the fault signal is cancelled.

The apparatus according to the invention exhibits a means for determining whether, with the same lambda value, the probe voltage is greater with the heater switched on than with the heater switched off, and for outputting the fault signal if this is the case.

BRIEF DESCRIPTION OF THE DRAWINGS

In the text which follows, the invention will be explained in greater detail with reference to embodiments illustrated by figures, in which:

FIGS. 4 to 7 show flowcharts relating to five embodiments for the condition step mentioned in FIG. 3;

DESCRIPTION OF THE PREFERRED EMBODIMENTS OF THE INVENTION

Figure 1:
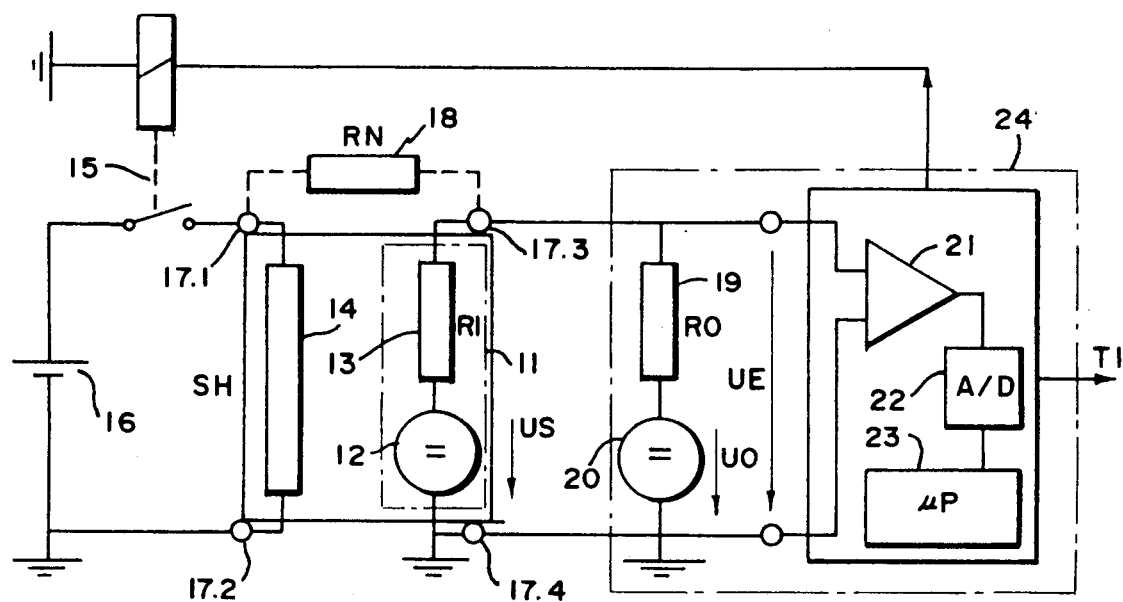
FIG. 1 shows a circuit diagram for a heatable probe with shunt and an evaluating circuit for the probe voltage.

In the circuit diagram according to FIG. 1, a lambda probe 11 is indicated by a dot-dashed box in which the redundant circuit of the probe is shown, namely a probe voltage source 12 which emits the probe voltage US, and an internal resistance 13 having the value RI. The lambda probe 11 is heated by a probe heater 14 which can be connected to a battery 16 via a switch 15 for this purpose. The lambda probe 11 and the probe heater SH 14 are located in a common housing having four terminals 17.1 to 17.4.

A fault case is assumed in which a shunt exists between the terminals 17.1 and 17.3 of heater 14 and probe 11, respectively, which are not connected to ground, which is represented by a shunt resistance RN 18 drawn as a dashed line.

The voltage US supplied by the probe 11, including the shunt voltage, is not directly tapped, but the tapping occurs at a load resistor 19 of resistance value RO which is connected to ground via a counter voltage source 20 of the voltage UO. The tapped voltage is designated by UE. This voltage is supplied via a differential amplifier 21 and an A/D converter 22 to a microprocessor 23 in a control device 24 where it is processed into a digital value and is evaluated in a closed-loop control method in order to, finally, become a measure of the fuel quantity to be metered, for example at an injection time TI. The switch 15 for the switching-on and switching-off of the probe heater 14 is also operated by the microprocessor 23. The switch is a separately controllable probe heating relay or a relay for controlling the fuel pump to which the probe heater is also connected. Electronic switching elements can also be used instead of relays.

Figure 2:
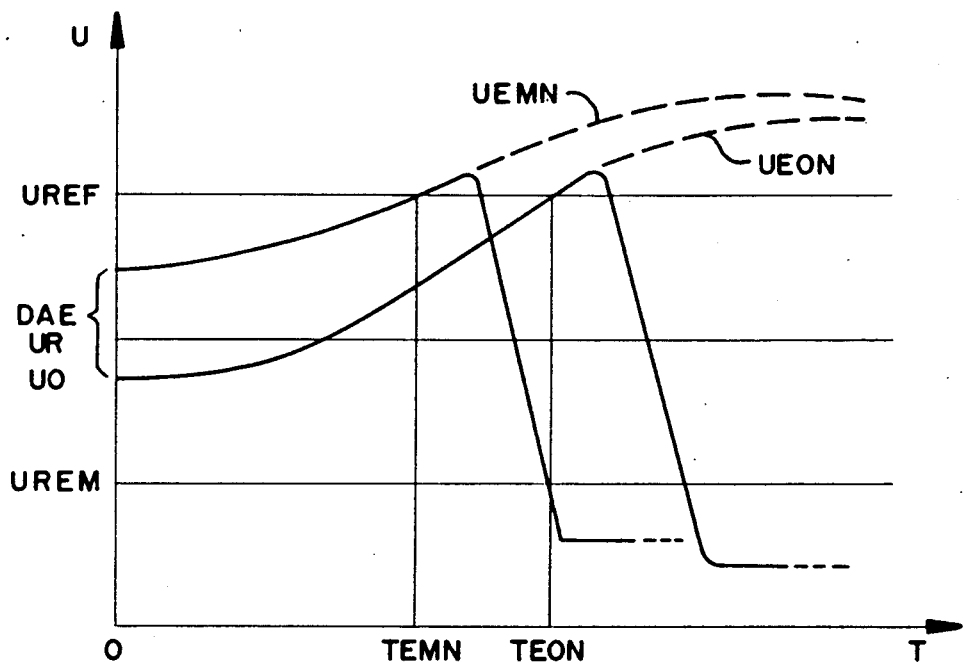
FIG. 2 shows a diagram for explaining various voltages which are of significance for the operation of a lambda probe.

FIG. 2 shows the input voltage UE as a function of time in the microprocessor 23 together with some other voltages. It must first be noted that two different curves are drawn for the input voltage, namely for an input voltage UEON without shunt and for an input voltage UEMN with shunt.

The curve of the voltage UEON without shunt will first be considered. When the lambda probe 11 is still cold, the internal resistance value RI is much higher than the load resistance value RO. The value of the input voltage UEON then corresponds to the counter voltage value UO. If, in contrast, the probe has reached its operating temperature, the internal resistance value RI is much lower than the load resistance value RO and the consequence is that the input voltage value UEON essentially corresponds to the probe voltage value US. The counter voltage value UO is selected such that it is located approximately in the middle between the probe voltage values US for rich and lean mixture. In FIG. 2 it is assumed that the probe is just being supplied with exhaust gas from a rich mixture. As the probe becomes warmer, the input voltage UEON therefore increases from the load voltage value UO towards higher voltage values.

If there is no shunt, the input voltage UEON with the probe heater switched on corresponds to the input voltage with the probe heater switched off. However, in FIG. 2 it is assumed that a shunt exists. The voltage UEMN is then higher than the voltage UEON, in fact by a difference value DAE when the heater is first switched on. FIG. 2 shows that the voltage UEMN, increased due to shunt, more and more approaches the voltage UEON as the time after the switching-on of the probe heater increases. The reason for this is that it has been assumed that the shunt is generated by water which, as a rule, is the case and that the water is more and more evaporated with increasing length of operation. In addition, the internal resistance greatly decreases with increasing warming of the probe, and the consequence is that the high-resistance shunt no longer has any great effect on the measurement result. As soon as the shunt or at least its influence is entirely eliminated, the voltage UEMN corresponds to the voltage UEON. The time until this is the case can be several minutes up to a few 10 minutes.

In FIG. 2, three threshold voltages are also drawn in, namely an upper threshold voltage UREF for rich lambda values, a lower threshold voltage UREM for lean lambda values and a reference voltage UR. If the voltage UE exceeds the voltage UREF or drops below the voltage UREM, the probe is detected as being ready for operation and is switched from open-loop control to closed-loop control. In the closed-loop control case, the direction of control is reversed in each case when there is an increase above or a drop below UR.

Accordingly, the threshold voltages UREF and UREM are used for the delayed switching-on of closed-loop control after an internal combustion engine is started. As explained above, the input voltage essentially only corresponds to the probe voltage when the internal resistance value RI has dropped below the load resistance value RO. It is only then that the measured values are usable for closed-loop control. Up to this time, several minutes can pass after the internal combustion engine has been switched on. From the switching-on of the engine up to the time at which the input voltage UEON with lacking shunt reaches the threshold voltage UREF, the time TEON passes. If, however, the input voltage UEMN is higher than the voltage UEON because of a shunt, the switching-on already occurs earlier, namely at the time designated by TEMN in FIG. 2. At this time, however, the probe is not yet sufficiently warmed up for operation so that unreliable closed-loop control results are obtained if closed-loop control is already permitted at this premature time. The switching-on of closed-loop control can be recognized in FIG. 2 by the fact that a jump occurs in the input voltage a short period after the times TEON and TEMN, respectively.

A method for detecting a shunt is now explained with reference to FIG. 3. It presupposes that the engine is stopped during the steps which are used for the detection (steps s1 to s5). After the method has been started, the probe input voltage UEHA is first measured in a step s1 with the heater switched off and the mean voltage value over 300 ms is formed. In a step s2, the heater is switched on and in a step s3, the input voltage UEHE is measured with the heater switched on and averaged. In a step s4, the difference DAE between the two voltages mentioned is determined. In a step s5, it is checked whether the difference DAE exceeds a threshold difference SDAE. If this is so, this corresponds to the outputting of a shunt signal which is indicated by a step s6. The confirmatory answer in step s5, that is the shunt signal, means that the probe is faulty, that is the lambda value should be switched on by an open-loop control.

After a marker A, step s6 is followed by a step s7 in which it is checked whether a shunt is still present. If this is so, the method returns to the marker A. If, in contrast, this is not so, a step s8 is reached via a marker B, in which a conventional readiness check is carried out, in the embodiment the readiness check according to the German publication mentioned initially.

This step s8 is also reached via the marker B starting from step s5 when it is found there that there is no shunt.

If it is found in the subsequent examination step s9 that the probe is not yet ready for operation, the method returns to the marker B. If, in contrast, the probe is ready for operation, this confirmatory answer in step s9 corresponds to the outputting of a closed-loop control readiness signal which is indicated by a step s10 which is reached via a marker C. The method ends with the emission of the closed-loop control readiness signal.

Figure 3:
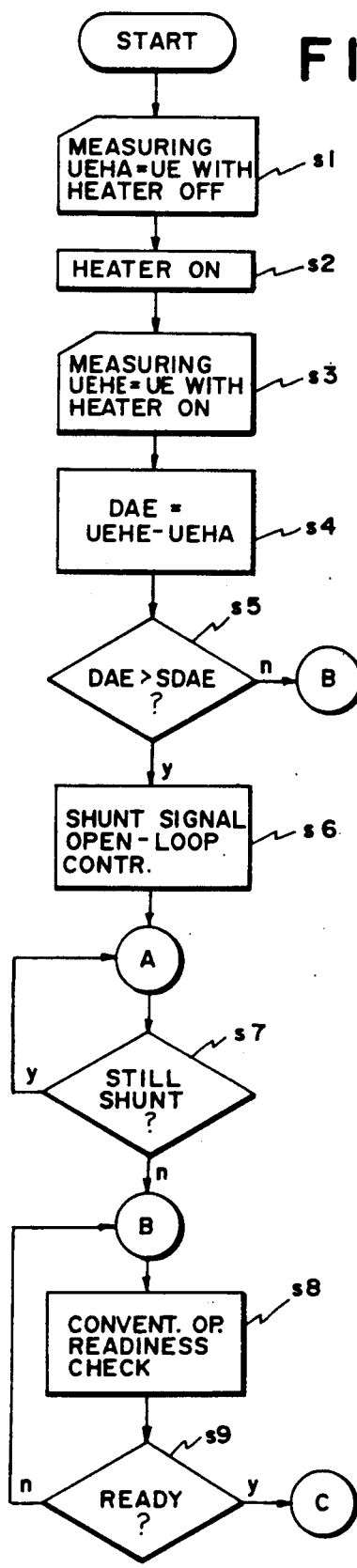
FIG. 3 shows a flowchart for explaining a method, which can be executed with a constant lambda value, for switching to open-loop control in the case of the presence of a shunt and for switching over to conventional checking for operational readiness after a predetermined condition has occurred.

The part methods according to FIGS. 4 and 5 deal with details of the sequence between markers A and B in FIG. 3.

In the part method shown in FIG. 4, it is checked in overrun phases whether a shunt is still present. For this purpose, it is initially checked in a step s4.1 whether overrun mode is present. If this is not so, the process returns to marker A. If, in contrast, overrun mode exists, a sequence is carried out in a sub-program step s4.2 which is equal to the process steps s1 to s4 of FIG. 3. A step s4.3 follows which is identical to step s5, that is it is investigated whether the voltage difference DAE exceeds the threshold difference SDAE. If this is so, shunt still exists which is why the method returns to the marker A. If, in contrast, there is no longer a shunt, the marker B is reached.

The part method according to FIG. 5 utilizes the observation that a shunt is caused, as a rule, by water which evaporates when the engine heats up. Thus, there should no longer be any shunt after a certain period of time has elapsed.

In the part sequence according to FIG. 5, the delay time TV for the switching-on is set to the value TV in a step s5.1 after the marker A. In a step s5.2, it is checked whether the measuring time T has already reached or exceeded the value of the delay time TV. As long as this is not so, step S5.4 will be carried out again and again. If, however, the condition is met, the lower method part according to FIG. 3 follows from the marker B.

The delay time TV can be a fixed value TVFIX. This has the advantage of a simple method sequence. However, there is the problem that different conditions cannot be taken into consideration. It must be assumed that, the higher the difference voltage DAE, the greater the delay time should be but that, on the other hand, the higher the current engine temperature TMOT, the shorter the delay time can be. The latter because it must be assumed that, in conjunction with the higher engine temperature, the environment of the probe also exhibits a higher temperature and thus water, which causes the shunt, evaporates more quickly.

The part methods according to FIGS. 6 and 7 in each case per se replace the part method of FIG. 3 between markers A and C. The check whether a shunt is still present is, at the same time, the check for readiness for closed-loop operation.

In the part method according to FIG. 6, it is investigated whether the probe input voltage UE with the heater switched on has dropped below a low threshold value UTIEF. If this is not so, the method returns to the marker A, and in the other case the marker C is reached. The low threshold value is determined such that the input voltage can only drop below it at typical operating conditions when the shunt voltage is no longer high. For example, the lowest probe voltage without shunt with the probe just operationally warm (about 300° C.) is determined for a predetermined configuration of internal combustion engine with lambda control. This voltage is assumed to be 100 mV for a particular arrangement. To this voltage, the tolerable shunt voltage is added, for example 50 mV. The added voltage of 150 mV is the low threshold value.

The part method according to FIG. 7 makes it possible to cancel the function of the shunt signal and, at the same time, to detect readiness for closed-loop control both when a lower threshold value and when an upper threshold value is reached. For this purpose, the voltage difference DAE is subtracted from the input voltage UEMN in a step s7.1. In a step s7.2, it is checked whether the voltage of UEK thus compensated to the correct value without shunt voltage has exceeded an upper threshold voltage UHOCH. If this is so, the marker C is reached. Otherwise, the method passes to a step s7.3 in which it is checked whether the uncompensated voltage UE has dropped below a lower threshold voltage UTIEF. If this is so, the method passes to marker C. Otherwise, the difference value DAE is lowered in a step s7.4 by a predetermined small value DDAE whereupon the part method again runs from marker A. The subtracted value DDAE does not need to be constant in time, but can change in such a manner that the change with time of the shunt (difference) voltage determined for typical cases is duplicated as accurately as possible.

Figure 7A:
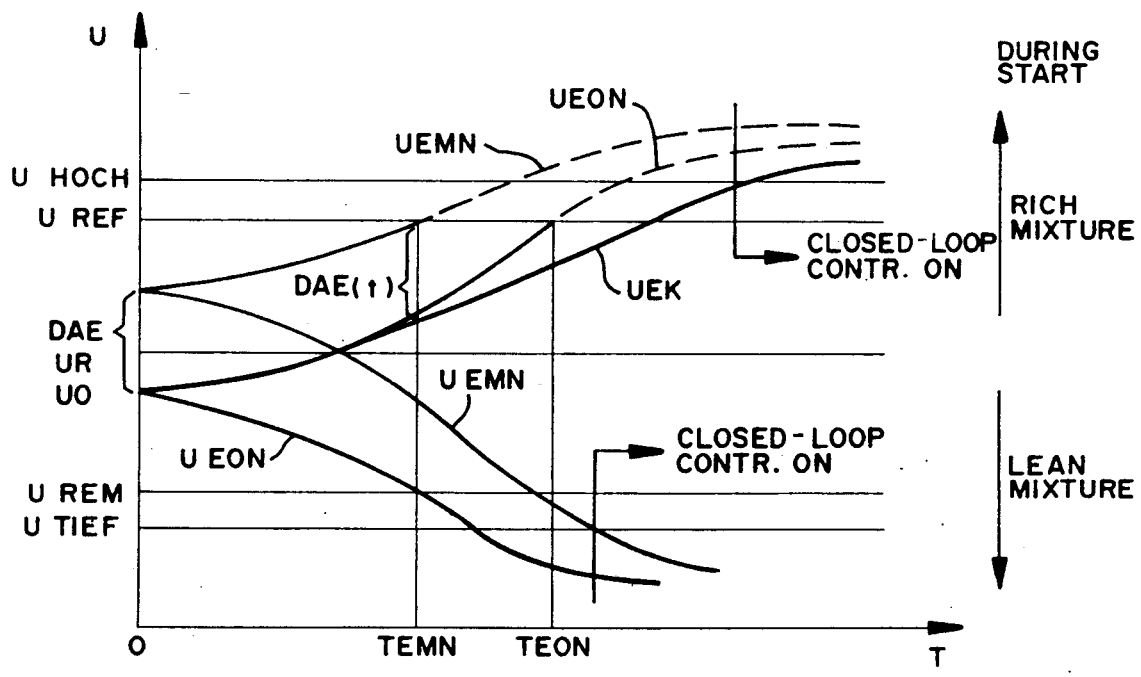
FIG. 7a shows diagrams of various voltages for explaining the method according to FIG. 7; and, FIG. 8 shows a flowchart for explaining a method, which can be executed with a variable lambda value, for switching to open-loop control in the case of the presence of a shunt.

FIG. 7a is used for explaining the method according to FIG. 7. In FIG. 7a, the variation of the input voltages UEMN and UEON for lean and rich (see also FIG. 2) air/fuel mixtures during the start of the internal combustion engine is specified. Furthermore, the variation of the compensated voltage UEK is shown.

The method shown in FIG. 7 replaces the part of the method of FIG. 3 between markers A and C. That is the method of FIG. 7 is only used when there is a shunt signal and the voltage UE is thus falsified by a shunt voltage in such a manner that it assumes higher values (UEMN).

As can be seen from FIG. 7a, a voltage thus falsified prematurely exceeds the upper threshold voltage UHOCH in the case of a rich air/fuel mixture when the internal combustion engine is being started and thus readiness for closed-loop control would be prematurely assumed. To prevent this, the compensated voltage UEK, which is calculated in step s7.1, is compared with UHOCH (s7.2) for the interrogation for readiness for closed-loop control.

In this connection, the difference DAE which is used for calculating UEK does not need to be constant with time, which is described by step s7.4 in FIG. 7 and is specified by DAE(t) in FIG. 7a.

DAE(t) represents the difference between UEMN and UEON at time t=0. This can be seen in FIG. 2 and follows from step s4 of FIG. 3 insofar as UEON-=UEHA with the heater switched off and UEMN-=UEHE with a shunt present and the heater switched on.

In the further course (t=0), however, this difference is not known and is only approximately reproduced by DAE(t). DAE(t) is determined such that UEK does not exceed the threshold value UHOCH too early, that is before the voltage UEON. That is, DAE(t) is thus normally greater than the true difference between UEMN and UEON for t=0, which also means that UEK extends below UEON.

If a lean air/fuel mixture is present when the internal combustion engine is being started, the comparison of UE with UTIEF is essential for the interrogation for readiness for closed-loop control.

Since, as has already been shown, the value DEA(t) is usually greater than the true difference between UEMN and UEON for t=0, the compensated voltage UEK-=UEMN−DAE(t) would extend below the voltage UEON. That is, on the other hand, that the lower threshold voltage UTIEF is reached too early in this case and readiness for closed-loop control would thus be assumed too early.

This is why the uncompensated voltage UE is used for the interrogation in step s7.3.

It should also be pointed out that the formulation in FIG. 7a "Closed-loop control on" is equivalent to that from step s7 of FIG. 3 in which a closed-loop control readiness signal is formed.

Figure 8:
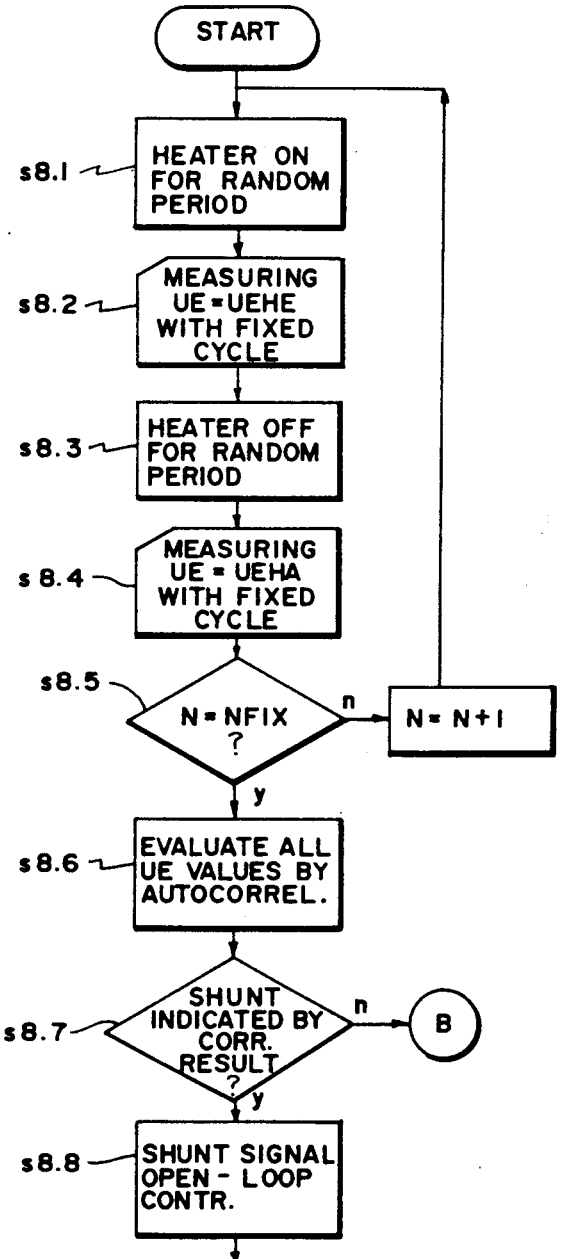

The part method according to FIG. 8 replaces that part of the method according to FIG. 3 which proceeds between the start and the marker A, that is the part method for detecting shunt and for outputting the shunt signal. This is a method which can also be carried out when the lambda value changes greatly with time so that it cannot be decided with only two successive measurement values which have been detected with and without heating whether a measured change has been caused by a change in lambda value or by a shunt.

In a step s8.1, the heater is switched on for a random period of time. In a step s8.2, the probe voltage UE-=UEHE is measured with the heater switched on during the entire period of time mentioned. In a step s8.3, the heater is switched off for a random period of time. During this period of time, the probe voltage UE is measured with a cycle which continues to be fixed, and this voltage, however, is now the respective voltage UEHA with the heater switched off. In a step s8.5, it is checked whether the number N which specifies how often steps s8.1 to s8.4 have been passed through, has already reached a predetermined number NFIX. If the number NFIX has not yet been reached, N is incremented by the value one and steps s8.1 to s8.4 are again carried out. The purpose of this sequence is to obtain sufficient measurement values for an autocorrelation method which is carried out in a step s8.6 when the number N reaches the predetermined number NFIX. In a step s8.7, it is checked whether the result of the autocorrelation method according to step s8.6 indicates the presence of a shunt voltage. If this is not so, the marker B of the sequence according to FIG. 3 is reached. If, in contrast, this is so, a shunt signal is output in a step s8.8 and the system is switched to open-loop control of the lambda value.

If a mathematically complex autocorrelation method is used, it is possible to find not only whether a shunt voltage is present or not, but its extent can also be determined. If the magnitude of the shunt voltage is established, it is subtracted from the measured probe voltage in order to provide by this means the actual correct probe voltage value. It is then not necessary to switch to open-loop control, but closed-loop control can be used with the aid of the correctly determined probe voltage value.

What is claimed is:

1. A method for detecting a fault condition of a lambda probe which can be heated by a probe heater and for taking measures in response to a fault signal which is emitted when the fault condition is detected, the method comprising the steps of:
   measuring the probe voltage with the heater switched off;
   switching the heater on;
   measuring the probe voltage with the heater switched on; and,
   issuing a fault signal when the measured values indicate the voltage to be greater when the heater is switched on than when the heater is switched off with each measured value being referred to the same lambda value.

2. The method of claim 1, wherein the method is carried out as long as the lambda value does not change such as before an internal combustion engine is started or during an overrun phase; and, the following further method steps are carried out:
   forming the difference between the measurement values; and,
   emitting the fault signal when the difference exceeds a predetermined threshold difference value.

3. The method of claim 1, wherein the method is carried out with a pseudo-binary switching-on/off sequence of the heater with changing lambda values; and, the following further method steps are carried out:
   measuring the probe voltage at a fixed cycle sequence; and,
   evaluating the measurement values by an autocorrelation process; and,
   emitting the fault signal when the evaluation indicates that a shunt voltage of inadmissible magnitude, which is independent of the particular lambda value, is superposed on the voltage values measured with the heater switched on.

4. The method of claim 1, wherein the lambda value is set by open-loop control during the presence of the fault signal.

5. The method of claim 1, wherein the action of the fault signal is cancelled after a predetermined period of time has elapsed after the occurrence of the fault signal.

6. The method of claim 5, wherein the period of time depends on the engine temperature at the time of the occurrence of the fault signal.

7. The method of claim 1, wherein the effect of the fault signal is cancelled when the probe voltage with the heater switched on drops below a predetermined low threshold value.

8. The method of claim 1, wherein, following the fault signal, a compensating voltage of an amount, which for example decreases over time, is subtracted from the probe voltage with the heater switched on, the compensating voltage initially exhibiting the value of the shunt voltage; and, the effect of the fault signal is canceled as soon as the compensated probe voltage exceeds an upper threshold value or the uncompensated voltage drops below a lower threshold value.

9. The method of claim 3, wherein, as long as the fault signal is emitted, closed-loop control is effected on the basis of a corrected probe voltage which is formed from the measured probe voltage by subtracting the shunt voltage obtained from an autocorrelation process.

10. Apparatus for carrying out a method for detecting a fault condition of a lambda probe, which can be heated by a probe heater, and for taking measures following a false signal which is emitted when the fault condition is detected, the apparatus comprising means for determining whether a probe voltage is greater with the heater switched on than with the heater switched off, in each case being referred to the same lambda value, and for emitting the fault signal if this is the case.

* * * * *